United States Patent [19]

Suh et al.

[11] Patent Number: 5,133,957
[45] Date of Patent: Jul. 28, 1992

[54] COMPOSITION AND METHOD FOR DESENSITIZING DENTIN

[75] Inventors: Byoung I. Suh, Oak Brook; Martin Hamer, Skokie, both of Ill.

[73] Assignee: Bisco, Inc., Itasca, Ill.

[21] Appl. No.: 761,667

[22] Filed: Sep. 18, 1991

[51] Int. Cl.$^5$ ............................................. A61K 6/08
[52] U.S. Cl. ........................................ 424/49; 106/35; 433/217.1; 433/228.1; 522/908; 523/115; 523/116; 523/118; 523/120
[58] Field of Search .................... 424/49–58; 106/35; 433/217.1, 228.1; 523/115, 116, 118, 120

[56] References Cited

U.S. PATENT DOCUMENTS

| | | | |
|---|---|---|---|
| 3,923,740 | 12/1975 | Schmitt et al. | 523/116 |
| 4,012,840 | 3/1977 | Takeuchi | 433/217.1 |
| 4,411,625 | 10/1983 | Koblitz | 523/116 |
| 4,437,836 | 3/1984 | Schmitz-Josten et al. | 433/217.1 |
| 4,459,193 | 7/1984 | Ratcliffe et al. | 523/116 |
| 4,514,527 | 4/1985 | Bowen | 523/115 |
| 4,521,550 | 6/1985 | Bowen | 525/116 |
| 4,588,756 | 5/1986 | Bowen | 523/116 |
| 4,813,876 | 3/1989 | Wang | 523/116 |
| 4,936,775 | 6/1990 | Bennett | 523/116 |
| 5,063,257 | 11/1991 | Akahane et al. | 523/116 |

FOREIGN PATENT DOCUMENTS 3610808 10/1986 Fed. Rep. of Germany.
2637181 4/1990 France.

OTHER PUBLICATIONS

Abadie et al C.A. 109:14478t (1988) of Bull. Soc. Chim. FR(1):20–24 (1988).
Saito et al C.A.109:79780e (1988) of JPN. 63063605 (Mar. 22, 1988).
Webb et al C.A.114:235013t (1991) of J. Dent. Res. 70(3):211–214 (1991).

Primary Examiner—Shep K. Rose
Attorney, Agent, or Firm—Marshall, O'Toole, Gerstein, Murray & Bicknell

[57] ABSTRACT

Hypersensitive dentin or cementum is treated by applying thereto two copolymerizable monomers which are polymerized in place and function to desensitize the hypersensitive areas. The first copolymerizable monomer used in the invention is the reaction product of N-phenylglycine or N-(p-tolyl)glycine and glycidyl methacrylate (NPG-GMA or NTG-GMA). The second copolymerizable monomer is selected from certain compounds produced by the reaction of an acid anhydride with excess hydroxyethyl methacrylate, e.g., biphenyl dimethacrylate. In a preferred embodiment, the mixture of monomers also contains a photosensitizer, such as camphoroquinone, which makes the mixture photocurable in addition to self-curable.

9 Claims, No Drawings

COMPOSITION AND METHOD FOR DESENSITIZING DENTIN

The present invention relates to a composition and method for desensitizing hypersensitive dentin and cementum.

BACKGROUND OF THE INVENTION

The problem of pain created in hypersensitive areas of dentin and cementum is quite common. The pain can be created in response to various stimuli on the surface of the teeth, such as thermal changes, changes in pH, contact with a brush or dental instrument, and other common circumstances which are difficult to avoid. The problem is especially acute in patients who have lost some of the normal protective enamel sheathing on tooth surfaces because of erosion, abrasion, caries, chipping of the enamel, or exposure of the dentin and cementum as a result of recession of the gums.

While the cause of pain from hypersensitive dentin or cementum has not been completely explained, a number of theories have been postulated. It is believed, however, that the cause of sensitivity is the degree of openness of the tubules in the area. It is postulated that displacement of the contents of the tubules under various conditions, as by contact of dentin with an air jet, scraping with a probe, temperature variation, or the application of a hypertonic solution causes the transmission of pain stimuli by a hydrodynamic flow to the nerve structure located in the pulp area. The link in the transmission of the stimuli is fluid in the tubules within the dentin, and in this connection, a relatively rapid movement of fluid outwardly from the pulp has been most clearly associated with pain.

In the past, there have been two approaches in attempts to solve the problem of eliminating pain in hypersensitive areas of the dentin and cementum. One method involves occluding the tubules by salt formation from an organic or inorganic acid, or other means intended to block the transmission of neural impulses from the dentinal surface to the dental pulp. U.S. Pat. No. 3,122,483 discloses the use of strontium ions for adsorption at the surface of odontoblastic fibrils or in the dentinal tubules to block the transmission of neural impulses. U.S. Pat. No. 3,863,006 discloses the use of potassium, lithium or sodium nitrites, in the form of an aqueous solution or a paste, for desensitizing hypersensitive dentin or cementum. U.S Pat. No. 4,057,621 discloses the use of mono- or di-substituted salts of an alkali metal or ammonium oxalate for desensitizing hypersensitive cementum. The salts are applied as an aqueous solution or a nontoxic paste.

As an alternative to sealing the dentinal tubules with salts some attempts have been made to use polymeric materials as a sealing medium. This expedient has met with only limited success, however, since it is very difficult to achieve adhesion of a polymeric film to living tissue such as dentin, especially under the moist conditions which exist in the mouth.

BRIEF DESCRIPTION OF THE INVENTION

In accordance with the present invention, it has been found that effective desensitization of hypersensitive copolymerizable monomers which are polymerized in place and function to desensitize the hypersensitive areas. Despite the moist conditions which exist in the mouth, the mixture of monomers used in the invention form, after copolymerization, a strongly adhering long-lasting protective film on the surface of the tooth, decreasing or eliminating hypersensitivity.

The first copolymerizable monomer used in the invention is the reaction product of N-phenyl-glycine or N-(p-tolyl)glycine and glycidyl methacrylate (NPG-GMA or NTG-GMA). These materials are aromatic tertiary amines having one carboxylic (—COOH) functional group attached to a carbon atom connected to a nitrogen atom. They have the unusual ability to cause the polymerization or copolymerization (self-cure) of another monomer molecule having one or more carboxylic functional groups.

The second copolymerizable monomer used in the invention is selected from certain compounds produced by the reaction of an acid anhydride with excess hydroxyethyl methacrylate. In a preferred embodiment, the mixture of monomers also contains a photosensitizer, such as camphoroquinone, which makes the mixture photocurable in addition to self-curable.

The monomers are applied to the affected areas of the tooth in solution in an appropriate solvent, which, in addition to being able to dissolve the monomer, must have at least a moderate degree of miscibility with water.

A preferred, but not essential, step in the method of the invention is pretreatment with a dentin conditioning agent, which is applied to the dentin before the application of the copolymerizable monomers. The conditioning agent is suitably a gel or semi-gel containing 1–50%, and preferably 5–15%, by weight of phosphoric acid. Any appropriate edible gelling agent, such as xanthan, guar, or tragacanth gums, can be used. With this concentration of acid, the smear layer of dentin is effectively removed for better bonding of the copolymerizable monomers, but the mineral portion of the dentin is not removed to any great extent.

DETAILED DESCRIPTION OF THE PREFERRED EMBODIMENTS

The first of the essential copolymerizable monomer (A) used in the invention (NPG-GMA and NTG-GMA) are the reaction products of N-phenyl glycine or N-(p-tolyl)glycine and glycidyl methacrylate, and are selected from compounds having the formula:

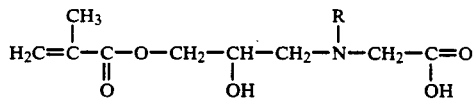

wherein

R is phenyl or p-toyl, and alkali metal (particularly lithium, sodium, or potassium) salts thereof.

The second copolymerizable monomer (B) is the reaction product of an acid anhydride with excess 2-hydroxyethyl methacrylate. The compounds useful in the invention are selected from those having the formulae

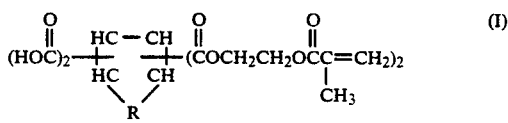

wherein R is oxygen or —$CH_2)_n$ and n is 0, 1, or 2;

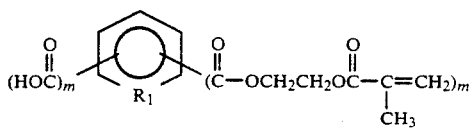 (II)

wherein $R_1$ is N or —CH= and m is 1 or 2;

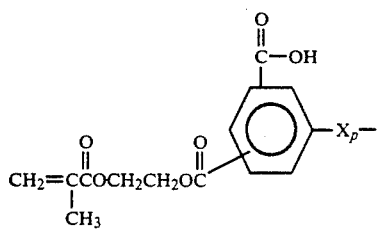 (III)

wherein
X is $$NR_2, O, S, SO, \overset{O}{\underset{O}{\overset{\|}{S}}}, \overset{O}{\overset{\|}{C}}, \overset{CF_3}{\underset{CF_3}{\overset{|}{C}}}, \text{ or } \overset{R_2}{\underset{R_3}{\overset{|}{C}}},$$

$R_2$ and $R_3$ are the same or different, and are selected from hydrogen and $C_1$–$C_3$ alkyl, and
p is 0 and 1;

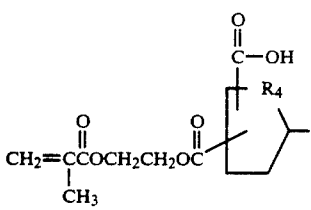 (IV)

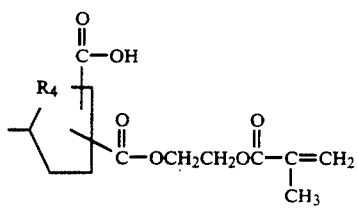

wherein
$R_4$ is —(CH$_2$)$_n$ and
n is 1 or 2;

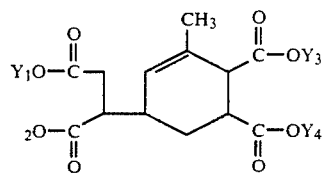 (V)

wherein one of $Y_1$ and $Y_2$ and one of $Y_3$ and $Y_4$ is hydrogen and the other is

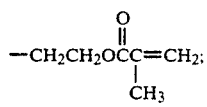

and

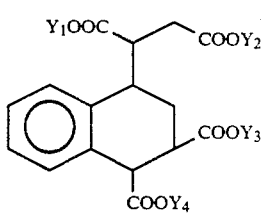 (VI)

wherein one of $Y_1$ and $Y_2$ and one of $Y_3$ and $Y_4$ is hydrogen and the other is

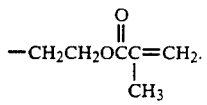

A preferred second monomer (B) for use in the invention is biphenyl dimethacrylate (BPDM) which corresponds to formula III in which p is 0.

All of the materials used as monomers A and B in accordance with the invention are readily available, or can be made in conventional manner from readily available reactants.

For application to a tooth in accordance with the invention, both of monomers A and B are dissolved in a solvent which must possess certain properties. In addition to dissolving the monomers, the solvent must have water-displacing properties, as evidenced by its ability to dissolve water to the extent of at least 25% of its own weight at room temperature. Preferably, the solvent is miscible with water in all proportions. In addition, the solvent desirably is fairly volatile, so that a small drop evaporates readily (within 30 seconds) at ambient temperatures. Examples of suitable solvents are acetone and $C_1$–$C_4$ alkanols, i.e., methanol, ethanol, propanol and butanol.

In the preferred embodiment of the invention, individual solutions of monomer A and monomer B are premixed to form a single solution which is applied to the area to be desensitized. The solution can contain about 1–50% by weight of combined monomers A and B, and preferably about 10–30%. The monomers are present in the solution in a weight ratio (A/B) of 1:1 to 1:50, and preferably 1:5 to 1:20. Application can be made by brush or swab or the like in an appropriate number of coats, typically two series of 3–4 applications, separated by a short (ca. 10 second) drying time.

The amount of monomer supplied should be sufficient to fill the tubules of the exposed dentin, as evidenced by the appearance of a glossy layer of monomer on the surface of the dentin after evaporation of the solvent.

As an alternative procedure, individual solutions can be applied as alternate layers to the tooth. In this case, the concentration of monomer in each solution can be selected such that the amount of monomers A and B deposited on the tooth surface falls within the ranges set out above when a single premixed solution is used.

In a preferred version of the invention, the solution of the second monomer (B) also contains an effective quantity, suitably 0.01–0.50%, of a photosensitizer such as camphoroquinone. The presence of the photosensitizer renders the reaction mixture quickly curable under the influence of an appropriate light source, even in the absence of a coinitiator, such as an aliphatic tertiary amine, which is typically used in light-cure formulations. In the absence of the photosensitizer, the mixture of the monomers will self-cure without a conventionally used catalyst, such as benzoyl peroxide, although more time may be necessary.

For convenience in carrying out the method of the invention, separate containers of monomer solutions can be supplied in kit form to be mixed shortly before use or applied consecutively to a tooth to be desensitized. Since the mixture of monomers in a single solution has a very limited life, however, it must be used within a short time.

The invention is illustrated by the following examples.

EXAMPLE 1

During her last dental examination, the patient reported extreme sensitivity of the mandibular right dentition to thermal changes and air fluctuations. Examination revealed exposed root surface of the mandibular right bicuspid due to gingival recession. The exposed root area was debrided and cleansed by gently scrubbing with a cotton pellet soaked in 4% chlorhexidine solution for 15 seconds. The exposed root surface was then thoroughly rinsed. The excess surface water was removed with a stream of air, leaving the dentin moist. A drop of monomer A solution (2% NTG-GMA in acetone) and a drop of monomer B solution (24% BPDM and 0.1% camphoroquinone in acetone) were mixed in a small well and applied by brush to the exposed root surface. Four coats of mixed monomer solution were applied and then dried for 5–6 seconds by a stream of air. Four additional coats of mixed monomers were then applied and again dried for 5–6 seconds by a stream of air. The deposited layer of monomers was then irradiated with a visible light-cure source for 10–20 seconds to finalize copolymerization of the monomers. The patient experienced immediate elimination of sensitivity to air fluctuations and thermal changes.

EXAMPLE 2

The patient reported extreme discomfort in the maxillary left anterior region of her oral cavity. Examination revealed a slightly abraded area of the root of the maxillary left canine. The exposed root area was cleansed and debrided with 10% phosphoric acid semi-gel for 10–15 seconds, after which the area was thoroughly rinsed with water. The excess water was removed by a stream of air, leaving the dentin moist. A mixture of monomer A solution and monomer B solution as in Example 1 was applied to the exposed root surface. Two series of four applications of the mixed monomers, separated by 5–6 seconds of drying time and followed by the same drying period were used. The monomer layer was irradiated with a visible light-cure source for 10–20 seconds to finalize the copolymerization of the monomers. The patient experienced immediate elimination of sensitivity.

EXAMPLE 3

The hypersensitve area of the tooth is cleaned by rubbing with a mixture of pumice and 10% phosphoric acid semi-gel for 10–15 seconds, after which the area is thoroughly rinsed. After air drying for 1–2 seconds, leaving the dentin moist, 3–4 coats of a monomer A solution containing 2% of NTG-GMA in acetone followed by 3–4 coats of a monomer B solution containing BPDM (16%) in acetone, followed by drying for 5–6 seconds. Another series of 4 coats of each monomer is applied, followed by drying. This monomer mixture is self-curing.

EXAMPLE 4

After preparation of the tooth area as in Example 3, a monomer A solution containing 2% NTG-GMA in acetone is applied in 3–4 coats followed by drying, after which a monomer B solution containing 24% BPDM and 0.1% camphoroquinone in acetone is applied in 3–4 coats followed by drying for 5–6 seconds. After a second series of coats of each of monomer A and B solutions is applied, the mixture of monomers is light-cured for 40 seconds under a visible light source.

The foregoing detailed description has been given for clearness of understanding only, and no unnecessary limitations should be understood therefrom, as modifications will be obvious to those skilled in the art.

What is claimed is:

1. A method of desensitizing hypersensitive dentin or cementum comprising applying to said dentin or cementum effective amounts of hydrophilic copolymerizable monomers A and B in solution in a water-displacing organic solvent, said monomers being applied simultaneously in a single solution or consecutively in separate solutions, and polymerizing said monomers to form an adhesive protective film thereon, monomer A being selected from the group consisting of the reaction products of N-phenyl glycine or N-(p-tolyl) glycine with glycidyl methacrylate, and alkali metal salts thereof, monomer B being selected from the group having the formulas

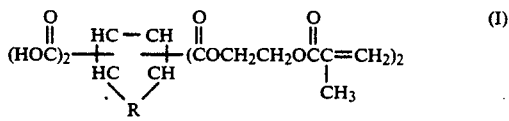

(I)

wherein R is oxygen or $-(CH_2)_n-$ and n is 0, 1, or 2;

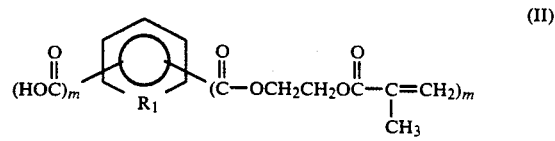

(II)

wherein $R_1$ is N or $-CH=$ and m is 1 or 2;

(III)

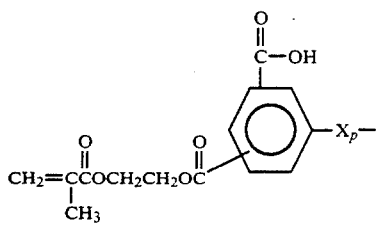

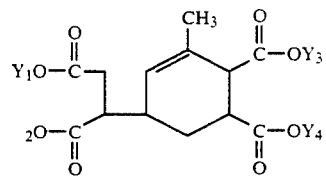

wherein one of $Y_1$ and $Y_2$ and one of $Y_3$ and $Y_4$ is hydrogen and the other is

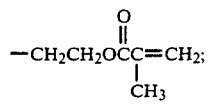

and

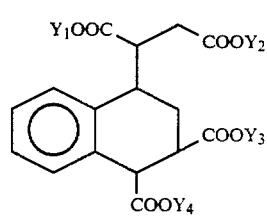

(VI)

wherein one of $Y_1$ and $Y_2$ and one of $Y_3$ and $Y_4$ is hydrogen and the other is

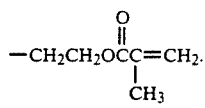

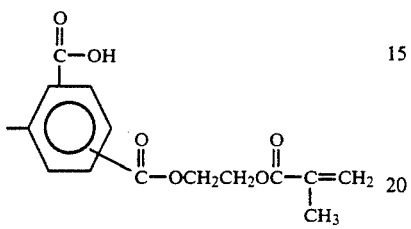

wherein

X is

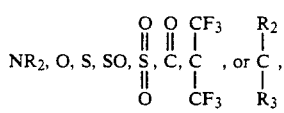

$R_2$ and $R_3$ are the same or different, and are selected from hydrogen and $C_1$-$C_3$ alkyl, and p is 0 or 1;

(IV)

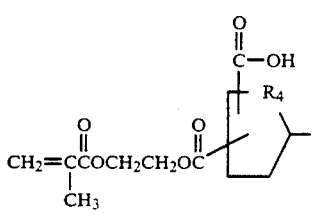

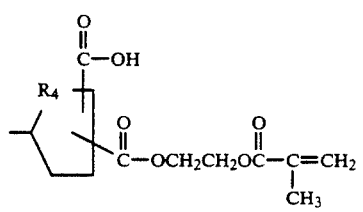

wherein $R_4$ is $-(CH_2)_n-$ and n is 1 or 2;

2. The method of claim 1 wherein said monomers are applied as a single solution containing 1-50% by weight of monomers A and B the weight ratio of monomer A to monomer B being within the range 1:1 to 1:50.

3. The method of claim 2 wherein said solution contains 10-30% by weight of monomers A and B, the weight ratio of monomer A to monomer B being within the range 1:5 to 1:20.

4. The method of claim 1 wherein said solvent is selected from organic solvents miscible with at least 25% by of water at ambient temperature.

5. The method of claim 3 wherein said solvent is selected from acetone and $C_1$-$C_4$ alkanols.

6. The method of claim 1 wherein at least one of said solutions contains in addition an effective amount of a photosensitizer whereby said monomers are rendered photocurable.

7. The method of claim 6 wherein said photosensitizer is camphoroquinone.

8. The method of claim 1 wherein said hypersensitive dentin and cementum are pretreated with a conditioning agent comprising 1 to 50% phosphoric acid prior to application of said monomers.

9. The method of claim 8 wherein said conditioning agent comprises 5 to 15% of phosphoric acid.

* * * * *